(12) United States Patent
Huang et al.

(10) Patent No.: US 10,544,178 B2
(45) Date of Patent: Jan. 28, 2020

(54) METAL COMPLEX COMPOUND AND PREPARING METHOD AND USAGE THEREOF

(71) Applicant: National Changhua University of Education, Changhua, Changhua County (TW)

(72) Inventors: Jui-Hsien Huang, Changhua (TW); Chi-Meng Hsiao, Changhua (TW); Jih-Hwa Guh, Taipei (TW)

(73) Assignee: National Changhua University of Education, Changhua, Changhua County (TW)

( * ) Notice: Subject to any disclaimer, the term of this patent is extended or adjusted under 35 U.S.C. 154(b) by 0 days.

(21) Appl. No.: 15/889,667

(22) Filed: Feb. 6, 2018

(65) Prior Publication Data
US 2019/0241592 A1    Aug. 8, 2019

(51) Int. Cl.
*C07F 15/00*    (2006.01)
(52) U.S. Cl.
CPC ................ *C07F 15/0046* (2013.01)
(58) Field of Classification Search
None
See application file for complete search history.

(56) References Cited

PUBLICATIONS

Lord et al. J. Med. Chem. 2015, 58, 4040-4053.*

* cited by examiner

*Primary Examiner* — Clinton A Brooks
(74) *Attorney, Agent, or Firm* — Muncy, Geissler, Olds & Lowe, P.C.

(57) ABSTRACT

A compound of formula (I) includes any forms of tautomer or stereoisomer thereof, wherein the formula (I) is presented as:

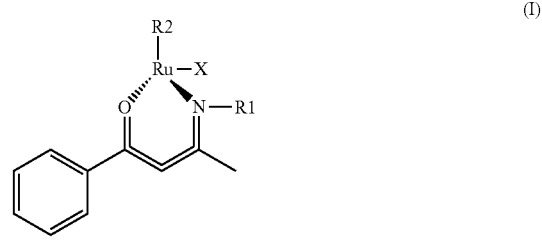

wherein the definitions of X, R1, and R2 are as specified in the specification hereof. The preparing method and the usage in cancer treatment of such compound are also provided by the present invention.

13 Claims, No Drawings

METAL COMPLEX COMPOUND AND PREPARING METHOD AND USAGE THEREOF

BACKGROUND OF THE INVENTION

1. Field of the Invention

The present invention relates to preparation of complex compound which is applied for cancer treatment, and more particularly, to a ruthenium metal complex compound and preparing method and usage thereof.

2. Description of the Related Art

A platinum complex compound Cisplatin is the most extensively researched medication for cancer treatment, which is able to restrain the activity of a variety of cancer cells and applied for curing various cancers, such as ovary carcinoma, testicular cancer, small cell lung cancer, and colorectal cancer (referring to the non-patent reference listed below).

However, as shown by clinical research, said medication made of Cisplatin is highly poisonous, which possibly damages cancer cells and normal cells simultaneously during the cancer treatment. In addition, Cisplatin causes metabolism acceleration and the compound production of inactive protein combination, so as to cause nephrotoxicity upon the patient. Therefore, researchers of relative fields aim at developing complex compound for replacing platinum metal.

Some researchers discovers that the geometric structure of ruthenium provides higher selectivity regarding the binding sites than the selectivity provided by platinum. Now, ruthenium made compound is mainly applied in catalysis field and photosensitizer. Also, ruthenium metal is found to be low poisonous. However, in the cancer treatment medication field, ruthenium metal made medication used for restraining certain type of cancer cells has not been developed.

Therefore, it is desirable to develop and apply the complex compound prepared with ruthenium metal for restraining activity of certain type of cancer cells, so as to be further applied in the cancer treatment filed.

Non-patent references: a) Y. W. Jung, S. J. Lippard, *Chem. Rev.* 2007, 107, 1387-1407; b) *Cisplatin—Chemistry and Biochemistry of a Leading Anticancer Drug* (Eds.: B. Lippert), VCHA, Zurich, Wiley-VCH, Weinheim, 1999, pp. 1-563; c) S. Dasari, P. B. Tchounwou, *Eur. J. Pharmacol.* 2014, 740, 364-78.

SUMMARY OF THE INVENTION

For improving the issues above, a metal complex compound and preparation method and usage thereof in accordance with an embodiment of the present invention are provided, wherein the metal complex compound is prepared with ruthenium metal. According to pharmacological research, ruthenium metal complex compound effectively restrains the activity of cancer cells.

For achieving the aforementioned objectives, a compound of formula (I) in accordance with an embodiment of the present invention is provided, comprising any forms of tautomer or stereoisomer thereof, wherein formula (I) is presented as:

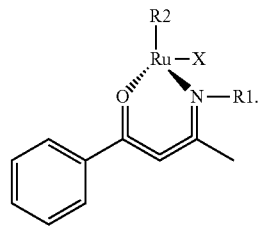

(I)

In formula (I), X refers to halogen atom such as chlorine (Cl), bromine (Br), or iodine (I). R1 refers to phenyl or substituted phenyl. R2 refers to 1-methyl-4-isopropyl benzene.

In another embodiment of the present invention, a preparing method of a compound of formula (I) is provided, comprising following steps:

mixing, wherein butyllithium (BuLi) and a compound of formula (II) are added into an organic solvent to be mixed to produce a reaction solution, wherein the formula (II) is presented as

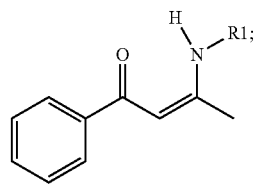

(II)

when the compound of the formula (II) and the BuLi are mixed, hydrogen ion of the compound of formula (II) is hydrolyzed to be replaced by lithium ion of the BuLi, so as to acquire a compound of formula (III), wherein the formula (III) is presented as

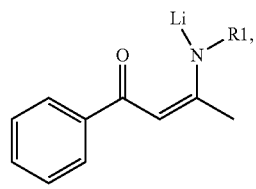

(III)

wherein R1 in the compound of the formula (II) and the compound of formula the (III) is defined according to the formula (I);

carrying out a titration reaction: wherein a compound of formula (IV) is applied as an initial material and mixed into the organic solvent, so as to form an initial solution, wherein the formula (IV) is presented as

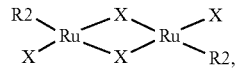

(IV)

wherein X and R2 in the compound of the formula (IV) is defined according to the formula (I); and adding the reaction solution into the initial solution having the compound of the formula (IV) in a manner of titration; during the titration of the reaction solution, stirring the initial solution for a stirring duration and extracting the initial solution by filtering, so as to acquire the compound of the formula (I).

In another embodiment of the present invention, a usage of compound of formula (I) or pharmaceutically acceptable salt thereof is provided, which is applied for preparing a medication for curing patients having at least one type of cancer, wherein the at least one cancer is prostatic cancer or breast cancer.

DETAILED DESCRIPTION OF THE INVENTION

The aforementioned and further advantages and features of the present invention will be understood by reference to the description of the preferred embodiment in conjunction with the accompanying drawings where the components are illustrated based on a proportion for explanation but not subject to the actual component proportion.

The terms "a", "an", and "the" presented in a singular form, unless clearly indicated to be otherwise in the context, also include the embodiment with plurality forms.

The term "about" or "approximate" used to indicate a certain parameter (such as reaching a molarity or temperature) includes embodiments within a ±10% difference range, preferably a ±5% difference range. For example, "1 molarity" is explained to be ranging from 0.8 to 1.2, preferably ranging from 0.9 to 1.1. When an element is cited to be applied in a purity "about" a certain percentage, the element is illustrated to be applied in a mathematical round-off integer and a scientifically acceptable value. For example, when an element is applied in a purity of 96%, the purity of the element ranges from 95.5% to 96.49%. As understood by people in the field of the present invention, when a parameter does not cause a critical difference, a number is usually applied only for clarity, not for limitation, of the embodiment.

A compound of formula (I) in accordance with an embodiment of the present invention is provided, comprising any forms of tautomer or stereoisomer thereof, wherein formula (I) is presented as:

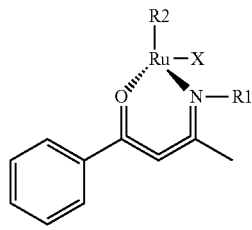

(I)

In the compound of formula (I):

The X refers to halogen atom such as chlorine (Cl), bromine (Br), or iodine (I); and The R1 refers to phenyl or substituted phenyl. R2 refers to 1-methyl-4-isopropyl benzene.

For example, R1 is allowed to be groups (i) to (iii) listed below:

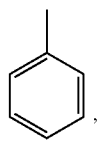
(i)

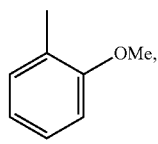
(ii)

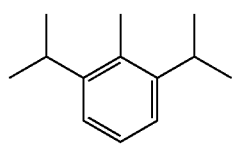
(iii)

It shall be understood that such groups are able to be presented in an optical active or racemic form. The formation of the optical activity is allowed to by synthesizing through the standard technique known in organic chemistry field, such as synthesizing through an optical actively initial material or analyzing the racemism. Similarly, the activity mentioned above is able to be assessed by use of standard laboratory technique.

In an embodiment of the present invention, X refers to chlorine atom.

Accordingly, in an embodiment of the present invention, the compound of formula (I) is:

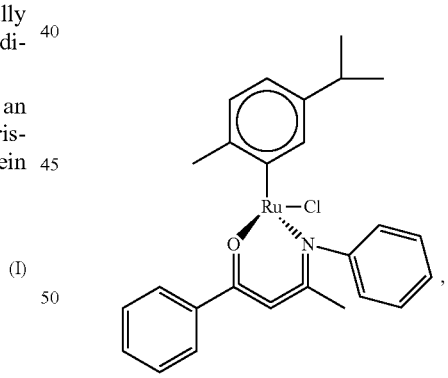

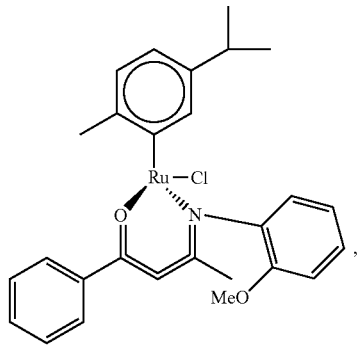

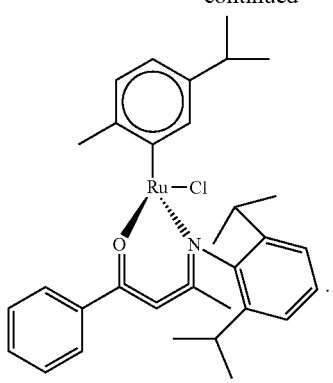

A preparing method of the compound of formula (I) in accordance with another embodiment of the present invention includes following steps: mixing, carrying out a titration reaction, and extraction.

In the mixing step, butyllithium (BuLi) and a compound of formula (II) are added into an organic solvent to be mixed to produce a reaction solution, and the reaction solution is cooled to a temperature ranging from 0 Celsius degrees to 22 Celsius degrees, wherein formula (II) is presented as

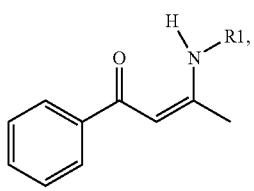
(II)

wherein the concentration of BuLi and the compound of formula (II) are the same. Also, the mass mixture ratio between the compound of formula (II) and BuLi ranges from 1:5 to 4:5. In a preferred embodiment of the present invention, the mass mixture ratio is 3:5. When the compound of formula (II) is mixed with BuLi, the hydrogen iron of the compound of formula (II) is replaced by the lithium iron of the BuLi, so that the compound of formula (III) is acquired, wherein the formula (III) is presented as:

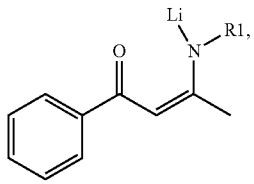
(III)

wherein the R1 of the compound with formula (II) and the compound with formula (III) is defined according to formula (I).

In the step of carrying out a titration reaction, a compound of formula (IV) is applied as an initial material and mixed into the organic solvent, so as to form an initial solution, wherein formula (IV) is presented as

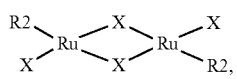
(IV)

wherein the concentration of the compound with formula (IV) ranges from 0.5 millimoles to 1 millimole, the R2 of the compound of formula (IV) is defined according to formula (I), and the organic solvent refers to tetrahydrofuran (THF).

In the step of extraction, the reaction solution is added into the initial solution having the compound of formula (IV) in a manner of titration, and the temperature of the initial solution is cooled to a range between 0 Celsius degrees to 22 Celsius degrees. Next, a hydrolysis substitution reaction is carried out upon the compound of formula (III) and the compound of formula (IV). During the titration of the reaction solution, the initial solution is stirred for a stirring duration and extracting the initial solution by filtering, so as to acquire the compound of formula (I), wherein the stirring duration ranges from 2 hours to 4 hours, and the compound of formula (I) is purified by use of a known isolation technique. According to the demand, the compound of formula (I) is allowed to be transformed into a pharmaceutically acceptable acid or base addition salt that is not isolatable, or isolated into isomer thereof through known isolation technique.

According to the pharmacological research, the compound of formula (I) is shown to be triggering the apoptosis, such that the apoptosis of cancer cells is re-activated for curing cancers, autoimmune diseases, and immune system diseases.

Particularly, the compound in accordance with the present invention is allowed to be applied for preparing medications used for treating patient having at least one cancers. According to primary research, the compound of the present invention effectively restrain prostatic cancer cells and breast cancer cells.

The illustration for preparing and applying the present invention does not limit the scope the present invention in any aspects.

Preparation 1: Compound of Formula (I), para-methylisopropylphenylchloride-1-carbonyl-3-n-phenyl-1-phenyl-2-butyleneruthenium (Ru(h⁶-cymene) (OCPhCHCMeNPh)Cl)

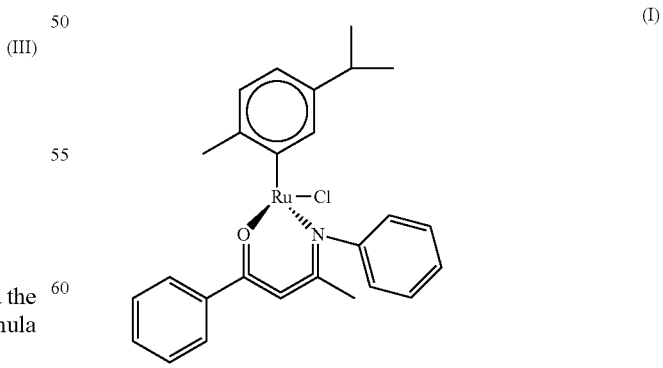
(I)

An amount of 0.51 ml of BuLi (1.26 mmol) and 0.3 g of 1-carbonyl-3-anilino-1-phenyl-2-butylene (OCPhCHC-MeNHPh) (1.26 mmol) are added into 15 ml of THF at a temperature of 0 Celsius degrees to form a reaction solution. Next, an amount of 0.39 g of dichloro(para-methylisopropylphenyl)ruthenium (Ru(h⁶-cymene)Cl₂) (0.63 mmol) is applied as the initial material and mixed with the THF at a temperature of 0 Celsius degrees to form the initial solution.

The reaction solution is added into the initial solution having dichloro(para-methylisopropylphenyl)ruthenium in a manner of titration. When the reaction solution is in the titration process, the initial solution is stirred and purified to be extracted and filtered with dichloromethane, so as to acquire the compound of formula (I), which is para-methylisopropylphenylchloride-1-carbonyl-3-n-phenyl-1-phenyl-2-butyleneruthenium, wherein the stirring duration is 3 hours.

¹H NMR (CDCl₃): 7.82-7.72 (m, 3H, benzene), 7.39-7.21 (m, 7H, benzene), 5.40 (s, 1H, CCHC), 5.32 (d, 1H, benzyne), 5.14 (d, 1H, benzyne), 5.03 (d, 1H, benzyne), 3.64 (d, 1H, benzyne), 2.66 (sept, 1H, CHMe₂), 1.99 (s, 3H, cymene Me), 1.76 (s, 3H, Me), 1.17 (m, 6H, CHMe₂)

Preparation 2: Compound of Formula (I'), para-methylisopropylphenylchloride-1-carbonyl-3-[(2-methoxyl) n-phenyl]-1-phenyl-2-butyleneruthenium (Ru(h⁶-cymene)[OCPhCHCMeN(Ph-2-OMe)]Cl)

(I')

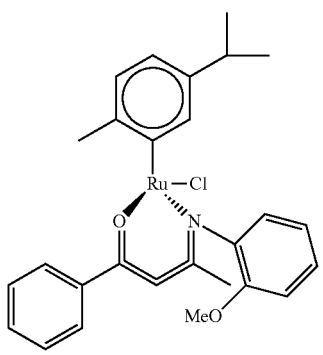

The preparing method is similar with the method in preparation 1. An amount of 0.45 ml of BuLi (1.12 mmol) and 0.3 g of 1-carbonyl-3-anilino-1-phenyl-2-butylene (OCPhCHCMeNHPh) (1.12 mmol) are added into 15 ml of THF at a temperature of 0 Celsius degrees to form a reaction solution. Next, an amount of 0.34 g of dichloro(para-methylisopropylphenyl)ruthenium (0.56 mmol) is applied as the initial material and mixed with the THF at a temperature of 0 Celsius degrees to form the initial solution. The reaction solution is added into the initial solution having dichloro (para-methylisopropylphenyl)ruthenium in a manner of titration, so as to acquire the compound of formula (I'), which is para-methylisopropylphenylchloride-1-carbonyl-3-[(2-methoxyl) n-phenyl]-1-phenyl-2-butyleneruthenium.

¹H NMR (CDCl₃): 7.83-7.74 (m, 3H, benzene, 7.30-7.18 (m, 4H, benzene), 6.99 (m, 2H, benzene), 5.41 (s, 1H, CCHC), 5.34 (d, 1H, benzyne), 5.16 (t, 2H, benzyne), 3.93 (s, 3H, OMe), 3.58 (d, 1H, benzyne), 2.66 (sept, 1H, CHMe₂), 1.97 (s, 3H, Me), 1.72 (s, 3H, cymene Me), 1.16 (t, 6H, CHMe₂)

Preparation 3: The Compound of Formula (I"), para-methylisopropylphenylchloride-1-carbonyl-3-[(2,6-diisopropyl)n-phenyl]-1-phenyl-2-butyleneruthenium (Ru(h⁶-cymene)[OCPhCHCMeN(Ph-2,6-ⁱPr₂)]Cl)

(I")

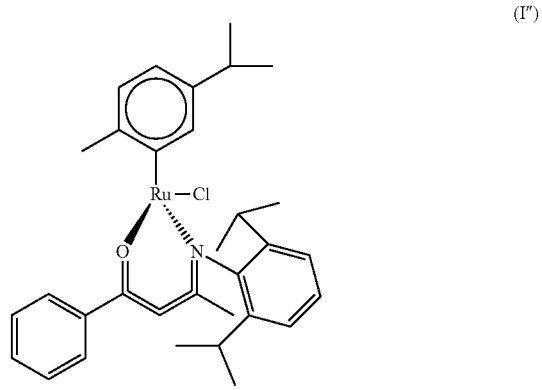

The preparing method is similar with the method in preparation 1. An amount of 0.41 ml of BuLi (1.02 mmol) and 0.3 g of 1-carbonyl-3-anilino-1-phenyl-2-butylene (OCPhCHCMeNHPh) (0.93 mmol) are added into 15 ml of THF at a temperature of 0 Celsius degrees to form a reaction solution. Next, an amount of 0.23 g of dichloro(para-methylisopropylphenyl)ruthenium (0.47 mmol) is applied as the initial material and mixed with the THF at a temperature of 0 Celsius degrees to form the initial solution. The reaction solution is added into the initial solution having dichloro (para-methylisopropylphenyl)ruthenium in a manner of titration, so as to acquire the compound of formula (I"), which is para-methylisopropylphenylchloride-1-carbonyl-3-[(2,6-diisopropyl)n-phenyl]-1-phenyl-2-butyleneruthenium.

¹H NMR (CDCl₃): 7.86-7.85 (m, 2H, benzene), 7.32-7.14 (m, 6H, benzene), 5.48 (s, 1H, CCHC), 5.35 (br, 2H, benzyne), 4.92 (d, 1H, benzyne), 4.18 (d, 1H, benzyne), 3.89 (sept, 1H, CHMe₂), 3.24 (sept, 1H, CHMe₂), 2.89 (sept, 1H, CHMe₂), 1.77 (s, 3H, cymene Me), 1.71 (s, 3H, Me), 1.37 (m, 12H, CHMe₂), 1.07 (t, 6H, CHMe₂)

Further, the present invention takes dichloro(para-methylisopropylphenyl)ruthenium (Ru(h⁶-cymene)Cl₂) as the initial material, and is able to produce several types of complex compounds having ruthenium metal through different chemical reaction, so as to realize medications for cancer treatments. The preparation methods are shown as Preparation 4 to Preparation 7.

Preparation 4: The Compound of Formula (V), para-methylisopropylphenylchloride-2-[1-para-tolueneimino]phenoxyruthenium ((Ru(h⁶-cymene)[o-OPhN=CH(Ph-4-Me)]Cl))

(V)

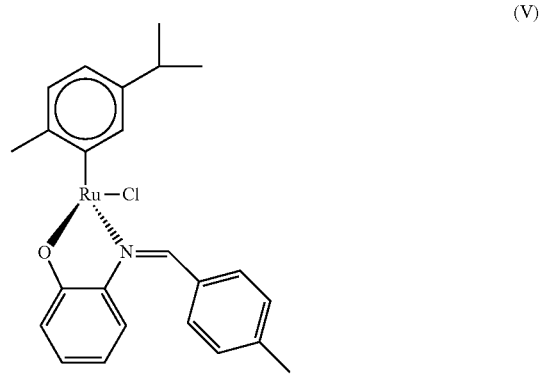

The preparing method is similar with the method in preparation 1. An amount of 0.42 ml of BuLi (1.05 mmol) and 0.2 g of 2-[1-para-tolueneimino]phenol (HOPh-[2-N=CH(Ph-4-Me)) (0.95 mmol) are added into 15 ml of THF at a temperature of 0 Celsius degrees to form a reaction solution. Next, an amount of 0.29 g of dichloro(para-methylisopropylphenyl)ruthenium (0.48 mmol) is applied as the initial material and mixed with the THF at a temperature of 0 Celsius degrees to form the initial solution. The reaction solution is added into the initial solution having dichloro(para-methylisopropylphenyl)ruthenium in a manner of titration, so as to acquire the compound of formula (V), which is para-methylisopropylphenylchloride-2-[1-para-tolueneimino]phenoxyruthenium.

$^1$H NMR (CDCl$_3$): 9.06 (s, 1H, N=CH), 8.15 (m, 2H, benzene), 7.35-6.94 (m, 5H, benzene), 6.40 (m, 1H, benzene), 5.33 (d, 1H, benzyne), 5.07 (d, 1H, benzene), 4.65 (d, 1H, benzyne), 4.47 (d, 1H, benzyne), 2.58 (sept, 1H, CHMe$_2$), 2.46 (s, 3H, Me), 2.21 (s, 3H, cymene Me), 1.06 (d, 6H, CHMe2)

Preparation 5: The Compound of Formula (V'), para-methylisopropylphenylchloride-2-[1-(2-naphthyl)azomethine] phenoxyruthenium (Ru(h$^6$-cymene)[o-OPhN=CH(C$_{-10}$H$_7$)]Cl)

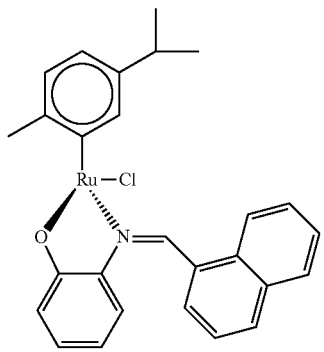

(V')

An amount of 0.066 g of sodium methoxide (NaOMe) (1.21 mmol) and 0.2 g of 2-[1-(2-naphthyl)azomethine]phenol (HOPh-[2-N=CH(C$_{10}$H$_7$))(0.81 mmol) are added into 15 ml of methanol to form a reaction solution which is stirred for 30 minutes. Next, an amount of 0.25 g of dichloro(para-methylisopropylphenyl)ruthenium (0.41 mmol) is applied as the initial material and mixed with the THF to form the initial solution.

Next, the reaction solution is added into the initial solution having dichloro(para-methylisopropylphenyl)ruthenium in a manner of titration to have a reaction under the room temperature. During the titration of the reaction solution, the initial solution is stirred for a stirring duration of 1 hour.

Next, the solution is stirred for 1 hour, and filtered and dried for removing sodium chloride, and the filtered solution is placed under a temperature of −20 Celsius degrees, so as to be recrystallized by use of saturated dichloromethane solution. Finally, a separation process is applied to acquire the compound of formula (V'), which is para-methylisopropylphenylchloride-2-[1-(2-naphthyl)azomethine] phenoxyruthenium.

$^1$H NMR (CDCl$_3$): 9.52 (s, 1H, N=CH), 8.72 (m, 1H, benzene), 8.02-7.66 (m, 6H, benzene), 7.50 (m, 1H, benzene), 7.03-6.95 (m, 2H, benzene), 6.47 (m, 1H, benzene), 5.33 (d, 1H, benzene), 5.00 (d, 1H, benzyne), 4.49 (d, 1H, benzyne), 3.79 (d, 1H, benzyne), 2.53 (sept, 1H, CHMe$_2$), 2.08 (s, 3H, cymene Me), 1.03 (d, 3H, CHMe$_2$), 0.96 (d, 3H, CHMe$_2$)

Preparation 6: The Compound of Formula (VI), para-methylisopropylphenylchloride-1-(para-diethylaminophenyl)-3-[(1-methyl-3-indazolyl)imino]-1-oxypropylruthenium (Ru(h$^6$-cymene)[N(CPhNNMe)CHOPhNEt$_2$]Cl)

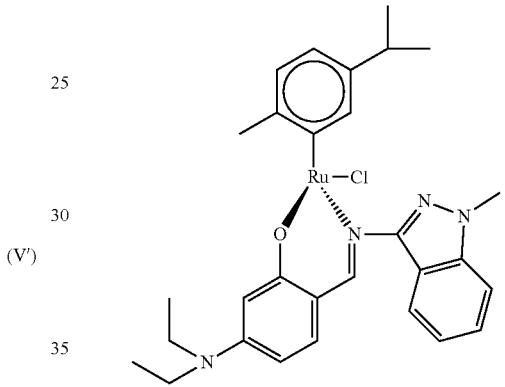

(VI)

An amount of 0.04 g of sodium methoxide (NaOMe) (0.74 mmol) and 0.2 g of 1-(para-diethylaminophenyl)-3-[(1-methyl-3-indazolyl)imin o]-1-propanol(N(CPhNNMe)CHOHPhNEt$_2$) (0.62 mmol) are added into 15 ml of ethanol to form a reaction solution which is stirred for 30 minutes. Next, the reaction solution is added into an initial solution having 0.38 g of dichloro(para-methylisopropylphenyl)ruthenium (0.62 mmol) in a manner of titration to have a reaction under the room temperature. During the titration, the reaction solution is stirred for a stirring duration of 3 hours.

Next, the solution is dried by use of magnesium sulfide to be solidified, wherein dichloromethane is removed. The acquired solid is placed under a temperature of −20 Celsius degrees, so as to be recrystallized by use of toluene solution. Finally, a separation process is applied to acquire the compound of formula (VI), which is para-methylisopropylphenylchloride-1-(para-diethylaminophenyl)-3-[(1-methyl-3-indazolyl)imino]-1-oxypropylruthenium.

$^1$H NMR (CDCl$_3$): 8.57 (d, 1H, benzene), 7.67 (s, 1H, benzene), 7.43-7.11 (m, 5H, benzene), 6.74 (d, 1H, benzyne), 6.17 (s, 1H, NCHC), 5.92 (d, 1H, benzyne), 4.99 (d, 1H, benzene), 4.08 (s, 3H, NMe), 4.04 (d, 1H, benzyene), 3.32 (sept, 4H, CH$_2$), 2.66 (sept, 1H, CHMe$_2$), 2.03 (s, 3H, cymene Me), 1.13 (m, 12H, Me)

Preparation 7: The Compound of Formula (VII), para-methylisopropylphenylchloride-2-(2-indazolyl) 1-phenyl-1-oxyethylruthenium (Ru(h⁶-cymene)(Ph-CNNCHOCPh)Cl)

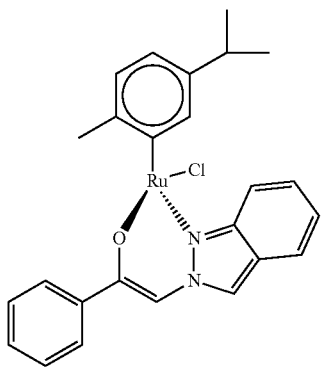

(VII)

An amount of 0.055 g of sodium methoxide (NaOMe) (1 mmol) and 0.2 g of 2-(2-indazolyl)1-phenyl-1-ethanone (PhCNNCH$_2$OCPh) (0.58 mmol) are added into 15 ml of methanol to form a reaction solution which is stirred for 30 minutes. Next, the reaction solution is added into an initial solution having 0.26 g of dichloro(para-methylisopropyl-phenyl)ruthenium (0.43 mmol) in a manner of titration to have a reaction under the room temperature. During the titration, the reaction solution is stirred for a stirring duration of 8 hours.

Next, the solution is dried by use of magnesium sulfide to be solidified, wherein dichloromethane is removed. The acquired solid is placed under a temperature of −20 Celsius degrees, so as to be recrystallized by use of dichloromethane/heptane solution. Finally, a separation process is applied to acquire the compound of formula (VII), which is para-methylisopropylphenylchloride-2-(2-indazolyl)1-phenyl-1-oxyethylruthenium.

$^1$H NMR (CDCl$_3$): 7.96-7.07 (m, 10H, benzene), 6.87 (s, 1H, NCHC), 5.54 (d, 1H, benzyne), 5.41-5.32 (m, 3H, benzyne), 2.73 (sept, 1H, CHMe$_2$), 2.01 (s, 3H, cymene Me), 1.17 (d, 3H, CHMe$_2$), 1.12 (d, 3H, CHMe$_2$)

Embodiment 1: The Compound of Formula (I), para-methylisopropylphenylchloride-1-carbonyl-3-n-phenyl-1-phenyl-2-butyleneruthenium Element microanalysis: (%, theoretical value, measured value)
% C=60.96; % H=5.49;% N=2.97

Embodiment 2: Compound of Formula (I'), para-methylisopropylphenylchloride-1-carbonyl-3-[(2-methoxyl) n-phenyl]-1-phenyl-2-butyleneruthenium Element microanalysis: (%, theoretical value, measured value)
%=58.89; % H=6.17; % N=2.41

Embodiment 3: the Compound of Formula (I"), para-methylisopropylphenylchloride-1-carbonyl-3-[(2,6-diisopropyl)n-phenyl]-1-phenyl-2-butyleneruthenium Element microanalysis: (%, theoretical value, measured value)
% C=66.28;% H=5.48;% N=2.93

Embodiment 4: The Compound of Formula (V), para-methylisopropylphenylchloride-2-[1-para-toluene-imino]phenoxyruthenium Element microanalysis: (%, theoretical value, measured value)
% C=61.74; % H=5.75; % N=3.08

Embodiment 5: The Compound of Formula (V'), para-methylisopropylphenylchloride-2-[1-(2-naphthyl)azomethine]phenoxyruthenium Embodiment 6: The Compound of Formula (VI), para-methylisopropylphenylchloride-1-(para-diethylaminophenyl)-3-[(1-methyl-3-indazolyl)imino]-1-oxypropylruthenium Element microanalysis: (%, theoretical value, measured value)
% C=56.49;% H=5.49;% N=8.46%

Embodiment 7: The Compound of Formula (VII), para-methylisopropylphenylchloride-2-(2-indazolyl)1-phenyl-1-oxyethylruthenium Pharmacology Research: cytotoxicity research upon PC-3 prostatic cancer and DU145 breast cancer Human cell HRMPC performing cell activity of PC-3 prostatic cancer and DU145 breast cancer is placed into PRMI1640 culture medium to be cultured under a temperature of 37° C. in a 5% CO$_2$/95% air. The PRMI1640 culture medium contains 10% FBS and penicillin (100 U/ml)/streptomycin (100 U/ml).

Afterward, the human cell HRMPC performing cell activity of PC-3 prostatic cancer and DU145 breast cancer is injected into embodiments 1 to 7 respectively, so as to carry out a comparison experiment analysis. Subsequently, the cell survivability is quantified through colorimetry (Sulforhodamine B Assay). In the experiment of the present invention, a conventionally known Cisplatin medication is applied as the control group.

The experiment result is performed with IC$_{50}$ (the compound concentration which is capable of restraining 50% of cell survivability) in Table 1.

TABLE 1

IC$_{50}$ of cytotoxicity of PC-3 cancer cell and DU145 cancer cell

| Items | SRB assay (GI$_{50}$, μM) | |
|---|---|---|
| | PC-3 Prostatic cancer cell (N = 3) | DU145 Breast cancer cell (N = 3) |
| Embodiment 1 | 5.66 ± 0.20 | 9.31 ± 1.48 |
| Embodiment 2 | 5.68 ± 0.12 | 14.34 ± 0.28 |
| Embodiment 3 | 2.39 ± 0.13 | 5.37 ± 0.06 |
| Embodiment 4 | 3.01 ± 1.17 | 13.06 ± 0.95 |
| Embodiment 5 | 4.58 ± 0.32 | 14.21 ± 0.35 |
| Embodiment 6 | >30 | >30 |
| Embodiment 7 | 29 (N = 1); >30 (N = 2) | >30 |
| Control group | 27.0 ± 6.1 $^a$ | 22.8 ± 5.1 |

As a result, embodiments 1 to 7 of the present invention perform obvious activity restraining effect upon PC-3 prostatic cancer cell and DU145 breast cancer cell, wherein the cancer cell restraining effect of embodiments 1 to 5 is significantly greater than the restraining effect of the control group. Therefore, the present invention proves that the complex compound prepared with ruthenium metal promotes the apoptosis, so as to achieve the cancer treating function. Also, the embodiments of the present invention are shown to enhance the cell activity restraining effect upon particular types of prostatic cancer cell and breast cancer cell, which is unexpected by the prior known Cisplatin medication.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A compound of formula (I), comprising any forms of tautomer or stereoisomer thereof, wherein the formula (I) is:

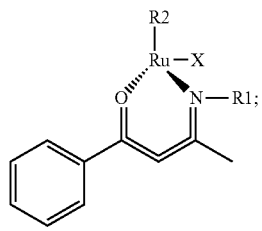
(I)

in formula (I):
the X is selected from the group consisting of chlorine (Cl), bromine (Br), and iodine (I); the R1 is

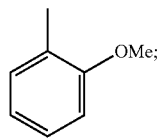

the R2 is 1-methyl-4-isopropyl benzene.

2. The compound of claim 1, wherein the X is chlorine atom.

3. A method of treating a patient having prostatic cancer and breast cancer, the method comprising treating the patient with the compound of claim 1 or pharmaceutically acceptable salt thereof.

4. A compound of formula (I), comprising any forms of tautomer or stereoisomer thereof, wherein the formula (I) is:

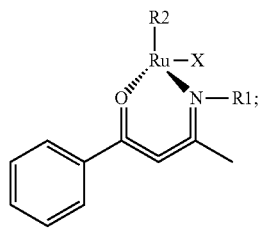
(I)

in formula (I):
the X is selected from the group consisting of chlorine (Cl), bromine (Br), and iodine (I); the R1 is

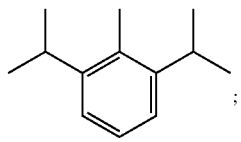
;

the R2 is 1-methyl-4-isopropyl benzene.

5. The compound of claim 4, wherein the X is chlorine atom.

6. A method of treating a patient having prostatic cancer and breast cancer, the method comprising treating the patient with the compound of claim 4 or pharmaceutically acceptable salt thereof.

7. A method of preparing a compound of formula (I), comprising any forms of tautomer or stereoisomer thereof, wherein the formula (I) is:

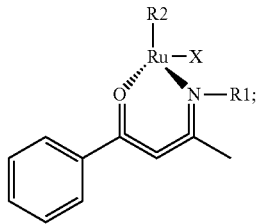
(I)

in formula (I):
the X is selected from the group consisting of chlorine (Cl), bromine (Br), and iodine (I); the R1 is

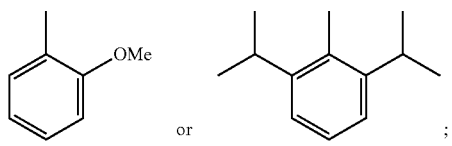

the R2 is 1-methyl-4-isopropyl benzene,
wherein the method comprises following steps:
mixing, wherein butyllithium (BuLi) and a compound of formula (II) are added into an organic solvent to be mixed to produce a reaction solution, wherein the formula (II) is presented as

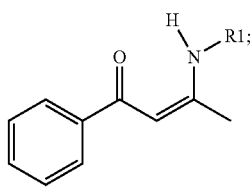
(II)

when the compound of the formula (II) and the BuLi are mixed, hydrogen ion of the compound of formula (II) is hydrolyzed to be replaced by lithium ion of the BuLi, so as to acquire a compound of formula (III), wherein the formula (III) is presented as

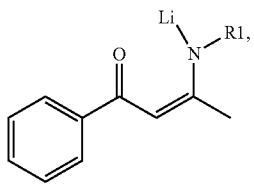

(III)

wherein R1 in the compound of the formula (II) and the compound of formula the (III) is defined according to the formula (I);

carrying out a titration reaction: wherein a compound of formula (IV) is applied as an initial material and mixed into the organic solvent, so as to form an initial solution, wherein the formula (IV) is presented as

(IV)

wherein X and R2 in the compound of the formula (IV) is defined according to the formula (I); and adding the reaction solution into the initial solution of the compound of the formula (IV) in a manner of titration, wherein during the titration of the reaction solution, the initial solution is stirred for a stirring duration and filtered to be extracted, so as to acquire the compound of the formula (I).

8. The method of claim 7, wherein during the titration reaction, the initial solution and the reaction solution are cooled down to a temperature ranging between 0 Celsius degrees to 22 Celsius degrees, so as to carry out a hydrolysis substitution reaction upon the compound of formula (III) and the compound of formula (IV) to acquire the compound of formula (I).

9. The method of claim 7, wherein during the titration reaction, a concentration of the compound of formula (IV) ranges from 0.5 millimoles to 1 millimole, and the stirring duration ranges from 2 hours to 4 hours.

10. The method of claim 9, wherein the concentration of the compound of formula (IV) is 0.63 millimoles, and the stirring duration is 3 hours.

11. The method of claim 7, wherein during the mixing step, a concentration of the compound of formula (II) ranges from 1 millimole to 1.5 millimoles; a concentration of the BuLi ranges from 1 millimole to 1.5 millimoles; and a mass mixture ratio between the compound of formula (II) and the BuLi ranges from 1:5 to 4:5.

12. The method of claim 11, wherein the concentration of the compound of formula (II) is 1.26 millimoles, and the concentration of the BuLi is 1.26 millimoles, such that the concentration of the compound of formula (II) is identical with the concentration of the BuLi.

13. The method of claim 11, wherein the mass mixture ratio between compound of formula (II) and the BuLi is 3:5.

* * * * *